United States Patent [19]

Agee

[11] Patent Number: 4,548,199
[45] Date of Patent: Oct. 22, 1985

[54] FRACTURE SPLINT

[76] Inventor: John M. Agee, 3980 Bartley Dr., Sacramento, Calif. 95822

[21] Appl. No.: 555,104

[22] Filed: Nov. 23, 1983

Related U.S. Application Data

[63] Continuation of Ser. No. 321,150, Nov. 13, 1981, abandoned, which is a continuation of Ser. No. 218,893, Dec. 23, 1980, abandoned, which is a continuation of Ser. No. 969,976, Dec. 15, 1978, abandoned.

[51] Int. Cl.[4] .............................................. A61F 5/04
[52] U.S. Cl. .................................................. 128/92 A
[58] Field of Search ................ 128/92 R, 92 A, 92 B, 128/92 BB, 92 D, 92 E, 84 B

[56] References Cited

U.S. PATENT DOCUMENTS

| 583,455 | 6/1897 | Bush | 128/92 D |
|---|---|---|---|
| 1,201,864 | 10/1916 | Overmeyer | 128/92 A |
| 1,789,060 | 1/1931 | Weisenbach | 128/92 A |
| 2,251,209 | 7/1941 | Stader | 128/84 B |
| 2,333,033 | 10/1943 | Mraz | 128/92 A |
| 2,393,831 | 1/1946 | Stader | 128/92 A |
| 2,434,431 | 1/1948 | Pincock | 128/92 A |
| 3,244,170 | 4/1966 | McElvenny | 128/92 B |
| 3,835,849 | 9/1974 | McGuire | 128/92 EB |
| 3,862,631 | 1/1975 | Austin | 128/92 B |
| 3,961,854 | 6/1976 | Jaquet | 128/92 A |
| 4,003,096 | 1/1977 | Frey | 128/92 C |
| 4,040,130 | 8/1977 | Laure | 128/92 R |

FOREIGN PATENT DOCUMENTS

| 863434 | 4/1941 | France | 128/84 B |
|---|---|---|---|
| 552075 | 4/1977 | U.S.S.R. | 128/92 A |

OTHER PUBLICATIONS

DePuy Mfg. Co. Catalog–p. 57, No Date.
Osteotaxis–External Fixation–Ad. in the Journal of Bone & Joint Surgery–Jan. 1977, vol. 59-A/1, p. 99.

*Primary Examiner*—John D. Yasko
*Attorney, Agent, or Firm*—Townsend and Townsend

[57] ABSTRACT

A fracture splint for setting fractures of the distal radius includes a distal member including a first stationary component and a first movable component pivotally pinned to the first stationary component, a proximal member including a second stationary component and a second movable component pivotally pinned to the second stationary component and a pair of intermediate, length-adjustment blocks slidably positioned along rods which extend between the distal member and the proximal member and being movable with respect to their correspondingly adjacent member by means of an adjustment screw. The distal member rigidly anchors a first surgical pin which passes through both metaphyseal corticies of the second metacarpal base and is received by the third metacarpal. The proximal member rigidly anchors two surgical pins which are inserted into the radial side of the radius perpendicular to the long axis of the radius. The first and second movable components and the adjustment screw and adjustment block arrangement permit the application of distraction forces in three directions independently of each other such that optimal length to the dorsal and radial aspects to the distal radius is restored.

1 Claim, 10 Drawing Figures

FRACTURE SPLINT

This is a continuation of Ser. No. 321,150, filed Nov. 13, 1981 abandoned which is a continuation of application Ser. No. 218,893, filed Dec. 23, 1980, abandoned which was a continuation of application Ser. No. 969,976, filed Dec. 15, 1978, abandoned.

BACKGROUND OF THE INVENTION

This invention relates in general to splints for fractures and in particular to splints associated with a fracture of the distal radius.

The proper setting of a fracture which will hopefully result in proper healing and rejoining of the bone sections may require a pin or other artificial device to be anchored into the bone sections so that the tendency of the bone sections to remain apart or misaligned can be overcome. Each bone fracture has its own unique alignment and healing aspects depending upon the bones which are involved, the size and health of the patient and the severity of the fracture. Fractures of the shaft or body portion of such bones as the femur, fibula, tibia, ulna and humerus can typically be set and will heal properly by means of an external plaster cast being applied. However, fractures in such areas as, for example, the neck of the femur or the proximal end of the ulna, usually necessitate the implanting of a pin or similar device in order to assure proper alignment of the bone sections during healing and to provide strengthening to the now-weakened bone portion.

The following listed patents provide a sampling of surgical apparatus designs associated with the setting of fractures which have been conceived.

| U.S. Pat. No. | Patentee | Issue Date |
| --- | --- | --- |
| 583,455 | Bush | 6/01/97 |
| 1,201,864 | Overmeyer | 10/17/16 |
| 1,789,060 | Weisenbach | 1/13/31 |
| 2,333,033 | Mraz | 10/26/43 |
| 3,244,170 | McElvenny | 4/05/66 |
| 3,835,849 | McGuire | 9/17/74 |
| 3,862,631 | Austin | 1/28/75 |
| 3,961,854 | Jaquet | 6/08/76 |
| 4,003,096 | Frey | 1/18/77 |
| 4,040,130 | Laure | 8/09/77 |

Bush discloses a surgical apparatus especially designed for securing together severed sections of broken knee-caps. The apparatus includes two members which are independently anchored into opposite bone sections and are coupled together by a threaded member.

Overmeyer discloses a surgical appliance wherein a plurality of bone-engaging pins are disposed along a bar. The pins are slidably adjustable both along the bar and in the direction normal to the bar such that bone sections on opposite sides of a fracture can be manually drawn together.

Weisenbach discloses a bone fracture clamp wherein a plurality of pins are anchored into the bone sections on opposite sides of the fracture. These pins are secured to specially arranged clamp members which may be moved up or down the length of the pins. The clamp members are joined together by means of a universal joint such that the position of the pins on one side of the fracture can be altered relative to the position of the pins on the opposite side of the fracture.

Mraz discloses a bone splint wherein a plurality of worm gear and pinion gear arrangements are provided for a variety of motions and adjustments between two different block members which support anchoring pins that are inserted into bone sections on opposite sides of a fracture.

McElvenny discloses a compression-type bone splint wherein two members which are independently anchored into opposite bone sections such that the bone sections may be drawn together. The splint is designed to preserve forcible engagement of the bone sections independently and irrespectively of the contracting action of the related muscles.

McGuire discloses a bone clamp for aiding a surgeon in positioning bones and securing them together. The bone clamp includes means for properly orienting drills so that aligned holes may be drilled through the two bone sections associated with a particular fracture, whereafter a screw may be inserted through the bones to hold them together.

Austin discloses a surgical implant for use at a site of bone fracture, especially at an osteotomy site, to draw the two parts of bone together and hold them together during healing. The implant is in the form of a staple having two legs to be driven into the bone, one on either side of the fracture. The two legs can be moved toward each other by means of a nut, once they have been driven into the bone.

Jaquet discloses an apparatus for orienting and securing a rod in a spatially adjusted position. The apparatus includes a U-shaped element having opposed parallel branches and a bottom portion connecting the branches. At least two superposed plates are disposed between the branches and the plates having mating faces with grooves therein cooperatively defining a hole receiving a rod. A flange is detachably secured to the branches of the U-shaped element to hold the plates and rod between the branches. The top plate is connected to the flange for rotation about an axis parallel to the branches and the bottom plate is rotatable with respect to the U-shaped element about the same axis.

Frey discloses a wrist joint endoprosthesis for positioning between the proximal joint part and the distal joint part in order to permit increased hand movements.

Laure discloses a wrist joint prosthesis for use as a replacement for the joint in a human wrist and which permits vertical motion, sidewise motion and rotary motion, but preventing twisting motion about an axis projecting from and parallel with the lower forearm. For this purpose, there is provided a metal socket fitted with a prong receivable into a bone of the forearm. A plastic cup made of material self-lubricating with respect to such metal socket is fitted within said socket, snappable thereinto to resist but not prevent withdrawal therefrom. Although Frey and Laure are not splint-type apparata, they are cited for their showing of surgical-related apparata associated with the bones of the wrist and forearm.

Although each of these various devices may have provided an improvement to what was known in the art at the time of their conception, there still remain certain types of fractures which present unique problems to medical personnel, and these fractures require a unique splint arrangement in order to achieve success in the setting and healing of the fracture. Consider, for example, the problems associated with a fracture of the distal radius, such as a Colles' fracture. With such a fracture, deforming, resting and working forces produced by the forearm muscles whose tendons pass across the fracture site, must be neutralized by the splint if the splint is going to be suitable for the setting of the fracture. It is important to the setting of such a fracture that the splint have a structural arrangement suitable to restore optimal length to the dorsal and radial aspects of the distal radius through distraction forces. However, due to the anatomy of the forearm, wrist and hand, in order to restore optimal length to the radius, the application of distraction forces in three different planes or directions is required. It is equally important that the degree or level of force applied in each plane or direction be adjustable separately and relatively independently of one another such that change of one force setting in one plane or axis will not have any substantial influence on the settings in a different plane or axis. The first required distraction force is applied in the direction of the radius along an axis which lies in a substantially parallel relationship to the long axis of the radius bone. The second required distraction force is applied in a torsional manner about the pronation-supination axis and effects a twisting motion at the fracture site. The third required distraction force is applied in a plane corresponding to radial-ulnar deviation of the hand with respect to the forearm. Motion in this third plane restores optimal length to the radial and dorsal aspects of the distal radius. The presence of three different force planes or force directions which may be independently adjusted to alter the twist, angular orientation or length of one bone fragment relative to the other bone fragment permits independent manipulation of the distal fragment with respect to the proximal fragment and permits achievement of optimal length for the setting of the fracture. A further consideration is that the splint must be anchored in some manner on the distal side of the fracture site and the use of a metacarpal bone provides a suitable anchoring position. This means that the hand orientation must be considered and accommodated for the particular splint design if the splint is going to be suitable for setting the fracture.

None of the disclosed devices of the listed patents provide these various structural features. Although the patent of Weisenbach might be considered relevant, its disclosed structure does not provide selective adjustment in three different directions because as soon as the bolt is loosened, the universal joint is unrestrained in all directions as is the location of the bolt in the slot. Thus, while trying to achieve one adjustment in one direction, the prior adjustments which may have already been set are lost or are in some way altered. A suitable splint for the fracture of the distal radius is one in which sufficient distracting forces can be applied in a minutely adjustable manner such that the variation of patient and patient fractures can be universally accommodated by a single device. Furthermore, as previously discussed, it is quite important that the three different directions of distracting forces be capable of separate and independent adjustment so that the physician and medical personnel assisting with the surgery do not have to continuously adjust and readjust a setting which is either not fixed or is attached when a subsequent setting is made.

SUMMARY OF THE INVENTION

A fracture splint for setting fractures of the distal radius according to one embodiment of the present invention comprises a distal member, first means for securing the distal member on the distal side of the radius fracture, a proximal member, second means for securing the proximal member on the proximal side of the radius fracture and means for joining the distal member to the proximal member. The joining means includes means for selectively varying the distance of separation between the distal member and the proximal member.

One object of the present invention is to provide an improved fracture splint for fractures of the distal radius.

Related objects and advantages of the present invention will be apparent from the following description.

DESCRIPTION OF THE PREFERRED EMBODIMENT

Figure 1:
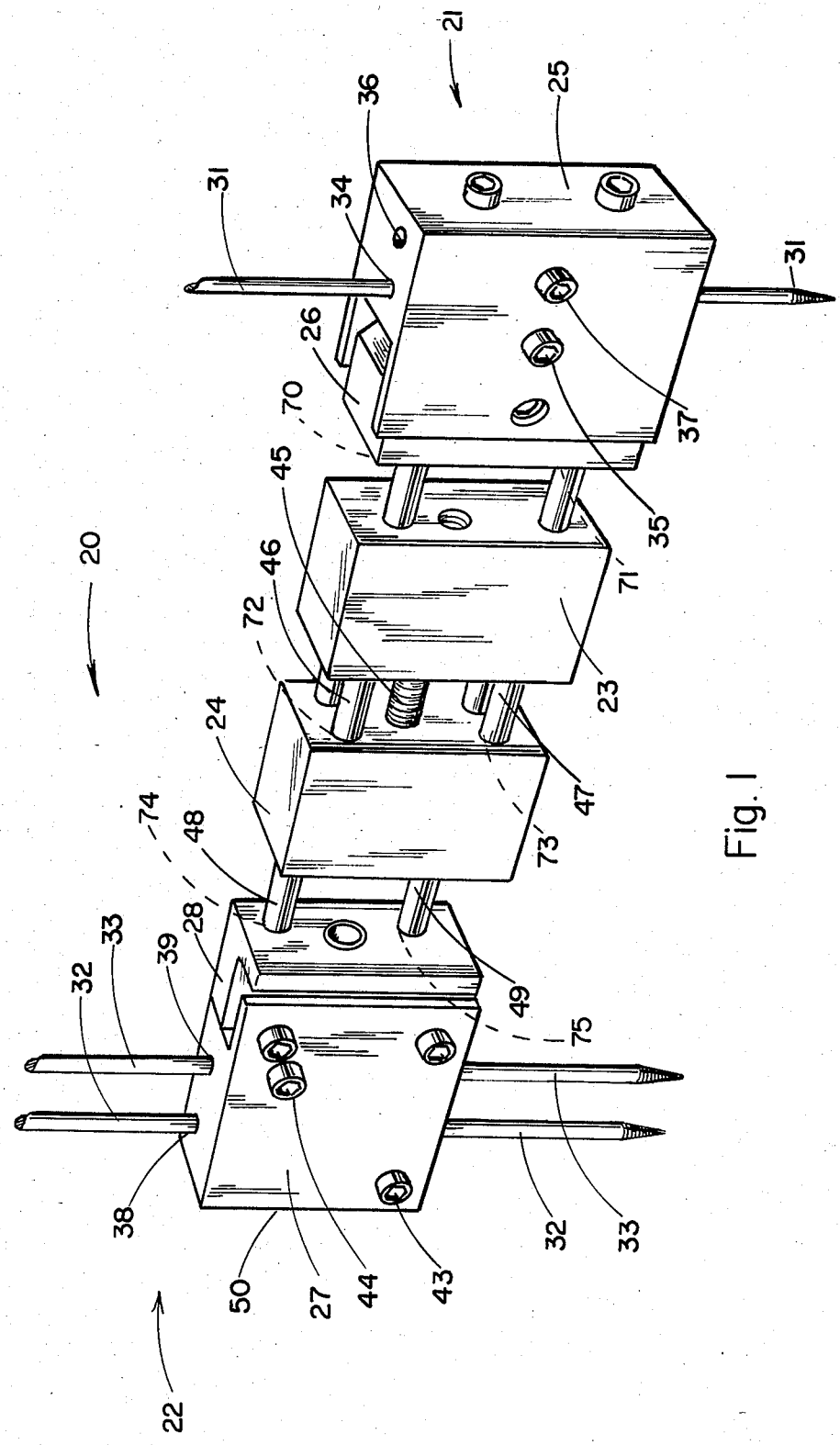
FIG. 1 is a fragmentary, perspective view of a fracture splint according to a typical embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to FIG. 1, there is illustrated a fracture splint 20 for use in positioning and setting a fracture of the distal radius. Fracture splint 20 includes a distal member 21, a proximal member 22, a distal adjustment block 23 and a proximal adjustment block 24. Distal member 21 includes a stationary component 25 which may be fabricated from aluminum or aluminum alloy or another similar light-weight, durable metal or plastic and a movable component 26 which may be fabricated from a material self-lubricating with respect to the metal of the stationary component such as "Nylon" or "Delrin" or similar synthetic material. Proximal member 22 includes a corresponding stationary component 27 which may also be fabricated from aluminum or an aluminum alloy or plastic and movable component 28 which is also constructed of a self-lubricating plastic material.

The orientation of fracture splint 20 in FIG. 1 corresponds to the orientation of the splint when used on the right forearm of the patient with the forearm, wrist and hand turned into a thumb-up position. This particular splint and hand orientation is illustrated in FIGS. 3-8 and it is to be understood that a similar arrangement could equally well be used for the left hand. The anchoring of fracture splint 20 to the forearm and hand of the patient is accomplished by means of surgical pins 31, 32 and 33. Surgical pin 31 extends through hole 34 in stationary component 25, and although pin 31 may slide through component 25, means are provided by way of allen head screw 35 to anchor pin 31 into stationary component 25 at a desired distance of separation between distal member 21 and the surface of the forearm. Also provided as part of stationary component 25 is a second clearance hole 36 and a second allen head screw 37. This additional hole and allen-head screw combination may be utilized in the event a second surgical pin is desired to be used in combination with stationary component 25. Similarly, pin 32 extends through hole 38 in stationary component 27 and pin 33 extends through hole 39. Pin 32 is anchored within stationary component 27 by means of allen head screw 43 and pin 33 is anchored by means of allen head screw 44. Surgical pins 31, 32 and 33 are externally threaded with coarse deep threads at one end and are also pointed with a cutting tip at the same end. The opposite end may be arranged with any number of gripping means so that the pins can be easily handled as well as providing a suitable drill-chucking surface for power driving the pins into corresponding bone portions for securely setting splint 20 as will be described in greater detail hereinafter.

Figure 2:
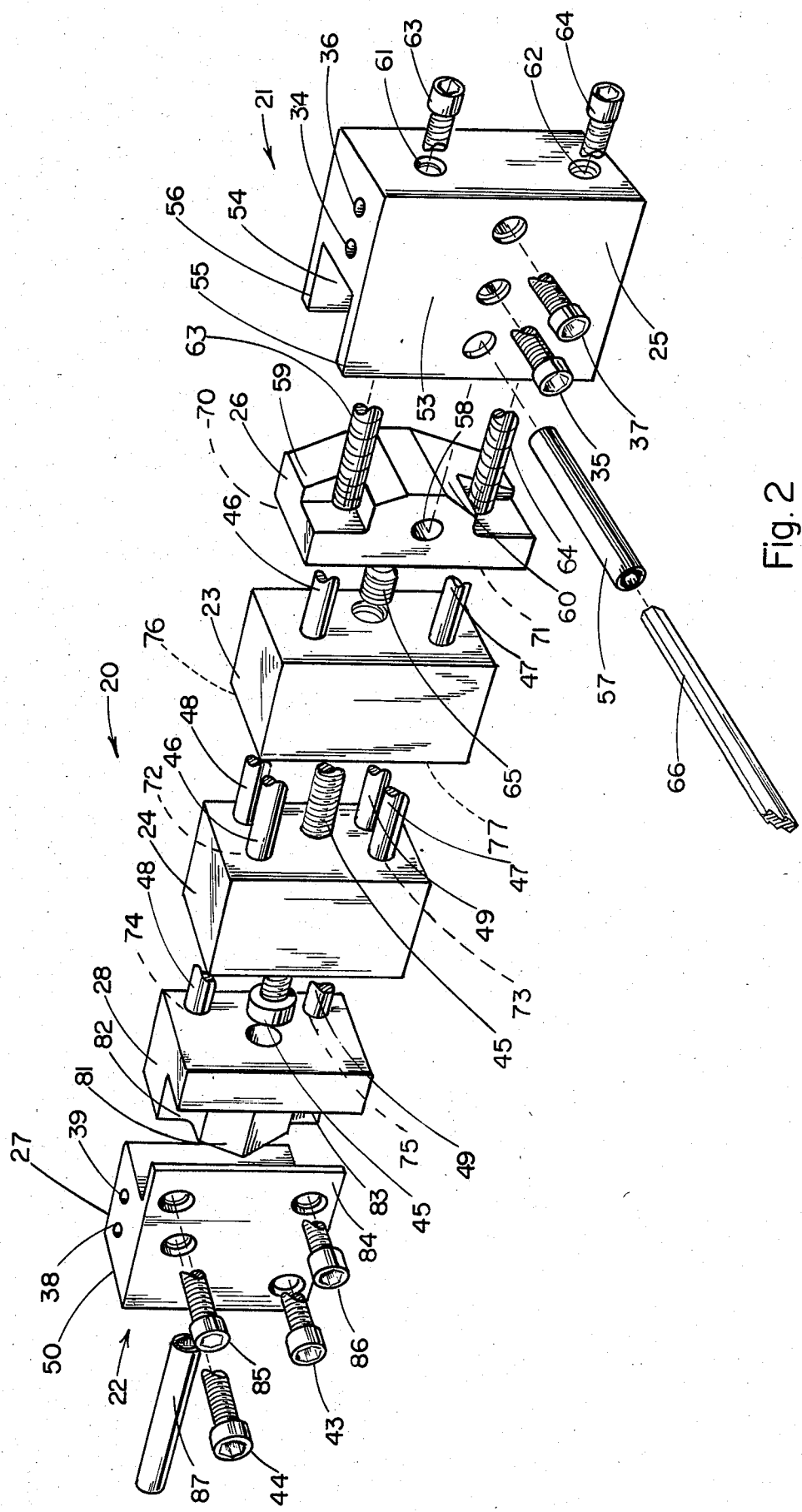
FIG. 2 is an exploded view of the FIG. 1 splint.
Figure 3:
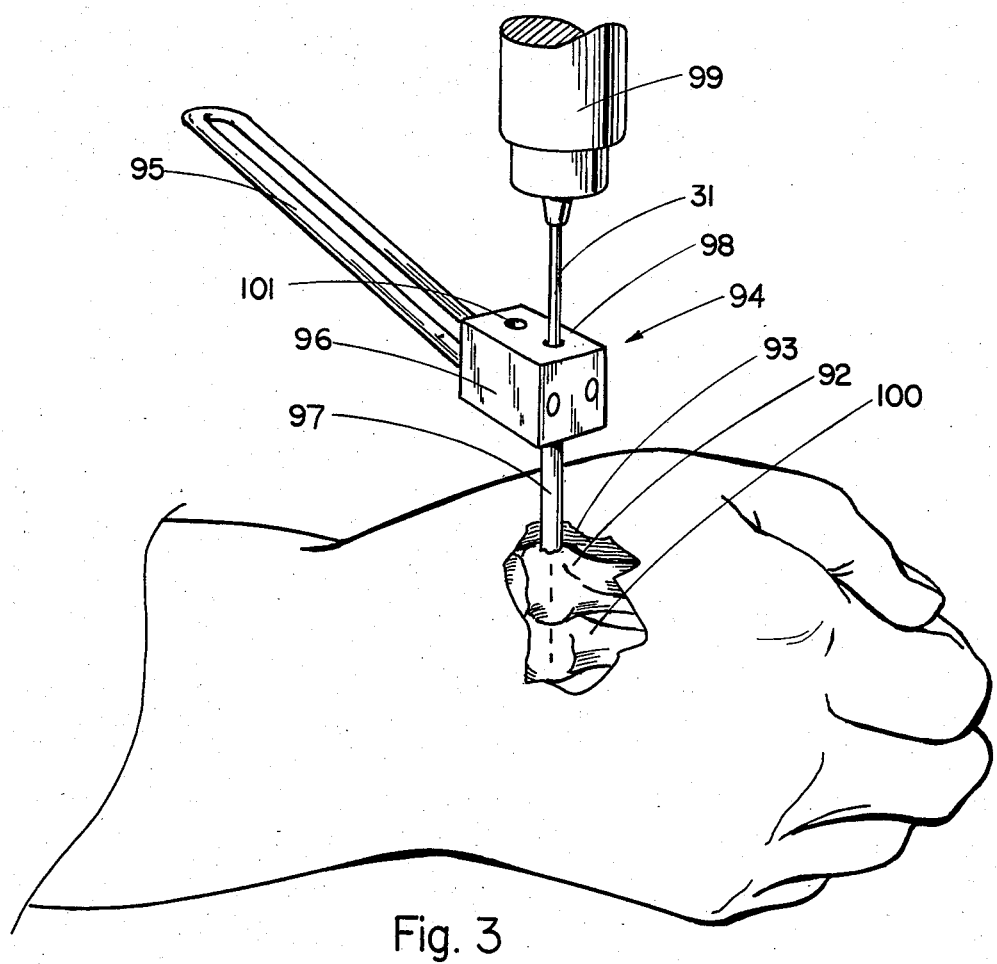
FIG. 3 is a partial perspective view of a surgical pin comprising a portion of the FIG. 1 splint and being inserted into metacarpal bones.

The length between distal member 21 and proximal member 22 is controlled by the arrangement of adjustment block 23, adjustment block 24, adjustment screw 45 and rods 46, 47, 48 and 49. The head of adjustment screw 45 is retained by adjustment block 24 and extends through block 24 and is threadedly received by adjustment block 23. Consequently, clockwise turning of adjustment screw 45 tends to pull adjustment block 24 toward adjustment block 23 as the adjustment screw 45 goes deeper into the internally threaded hole extending through block 23. Rods 46-49 are arranged in a four-corners orientation, however, all four rods do not extend the full length from movable component 26 to movable component 28. Rather, there is a staggered relationship wherein rods 46 and 47 are received by movable component 26 and extend through adjustment block 23 and are then received by adjustment block 24. Similarly, rods 48 and 49 are received by movable component 28 and extend through adjustment block 24 and are received by adjustment block 23. There is a clearance hole originating at the outermost end 50 of the proximal member 22 which extends completely through stationary component 27 and movable component 28 such that a suitable allen wrench may be extended through this clearance hole in order to reach the head of adjustment screw 45. Then, as adjustment screw 45 is turned in a clockwise direction, the overall length between movable component 26 and movable component 28 will increase. This lengthening procedure of splint 20 is important in that splint 20 is initially installed in a contracted position and must thereafter be lengthened to restore optimal length to the radius as a necessary step in the surgical procedure. The intricacies of the design of the various members and components and their relationship to one another can better be illustrated by referring to FIG. 2 which is an exploded view of the FIG. 1 fracture splint, excluding pins 31, 32 and 33, and shows the surface contour of stationary component 25 relative to movable component 26 and of stationary component 27 relative to movable component 28. These specialized surface contours are important in order to permit alignment and orientation adjustments independently and in two different directions as may be critical for the proper setting of the radius fracture.

Figure 7:
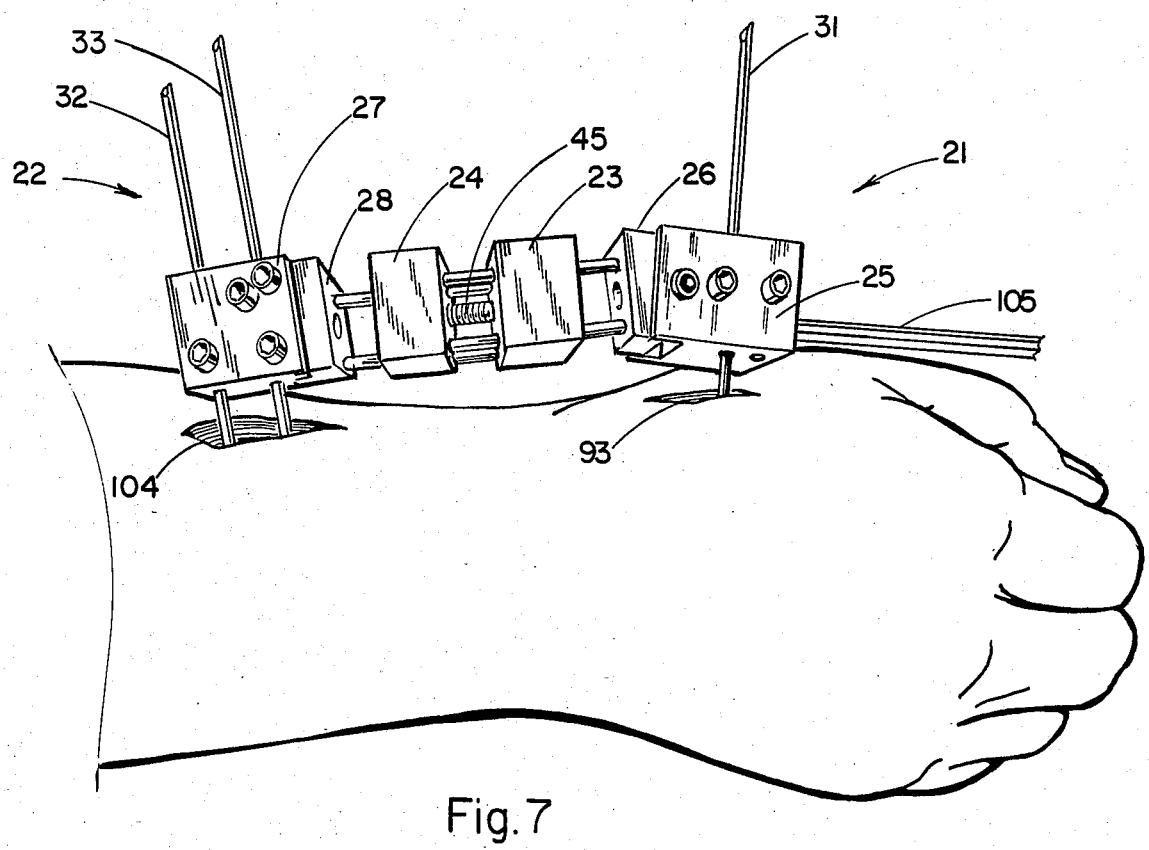
FIG. 7 is a fragmentary, side elevation view of the FIG. 1 splint illustrating adjustment of radial-ulnar deviation.

Stationary component 25 includes a main body portion 53 through which holes 34 and 36 extend as well as allen head screws 35 and 37. The end of stationary component 25 which is interior fracture splint 20 is segmented by rectangular slot 54 into two side members 55 and 56. Extending through these two side members without any interference fit, tubular pivot pin 57 passes through hole 58 in movable component 26 in a force fit manner, being retained therein by set screw 65. The hollow inside of pin 57 is a convenient receptacle for the storage of a typical L-shaped allen wrench 66. The short end of the wrench is retained in pin 57 with the long end of the wrench being secured to the splint with adhesive tape. Although generally a rectangular solid, movable component 26 is contoured along one edge with tapered sides 59 and 60 and corresponding spot-faced surfaces which are aligned with internally threaded holes 61 and 62, respectively, in stationary component 25. Allen head screws 63 and 64 extend through holes 61 and 62 and abut against the spot-faced surfaces of tapered sides 59 and 60. Inasmuch as movable component 26 is initially free to rotate with tubular pivot pin 57 on stationary component 25, one of the two allen head screws 63 or 64 is used to set the direction and extent of pivotal rotation while the other allen head screw is utilized as a rigid stop to prevent rotation beyond the desired point. Therefore, allen head screws 63 and 64 cooperatively act together as positioning means and retaining means for a selected rotation of movable component 26 relative to stationary component 25. This plane of rotation about the axis of tubular pivot pin 57 corresponds to the plane of radial-ulnar deviation as is illustrated in FIG. 7. By means of a suitably sized allen wrench such as allen wrench 66 or allen wrench 105, screws 63 and 64 may be set to the proper deviation orientation as governed by the nature of the fracture. By firmly securing screws 63 and 64 against component 26, a locking mechanism is achieved to secure the degree of radial-ulnar deviation that has been demonstrated to be optimal. The internal hollow portion of tubular pivot pin 57 is utilized as a storage chamber for a suitable allen wrench 66 which has a proper hex size dimension for all of the allen head screws employed as part of fracture splint 20.

Movable component 26 also includes two blind holes 70 and 71 which extend into movable component approximately 0.37 inches. Received by these two blind holes are rods 46 and 47 which extend through block 23 and are correspondingly received by two blind holes 72 and 73 in block 24. These holes are also approximately 0.37 inches in depth. Movable component 28 also includes two blind holes 74 and 75 which are approximately 0.37 inches in depth and receive rods 48 and 49. Rods 48 and 49 extend through block 24 into block 23 where they are received by blind holes 76 and 77. Rods 46 and 47 establish the distance of separation between movable component 26 and block 24 while rods 48 and 49 establish the distance of separation between movable component 28 and block 23. Consequently, as block 24 moves away from movable component 28, this causes movable component 26 to also move farther away from movable component 28. Similarly, as block 23 moves away from movable component 26, movable component 28 also moves farther away from movable component 26. What is actually occurring is that as screw 45 is turned in a clockwise direction, drawing blocks 23 and 24 closer together, the degree of this compression corresponds to an identical distraction separation of movable component 28 and movable component 26.

Figure 8:
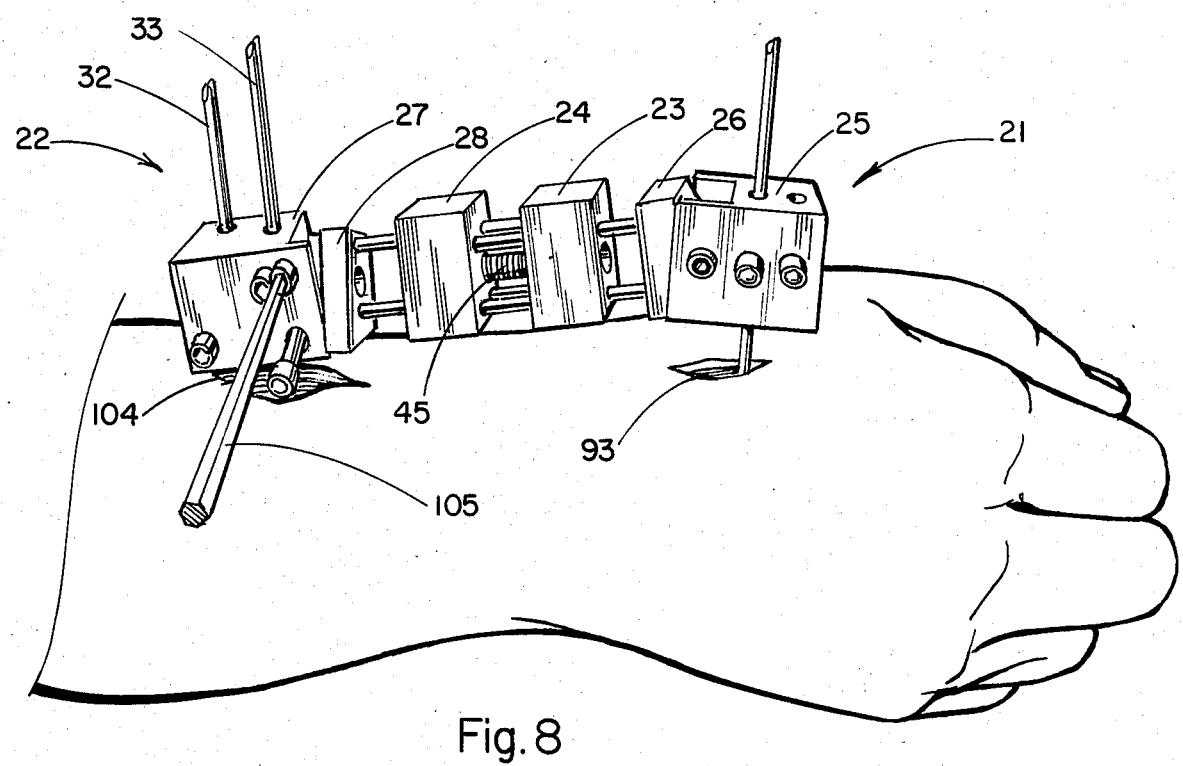
FIG. 8 is a fragmentary perspective view of the FIG. 1 splint illustrating pronation of the hand, wrist and distal fragment relative to the proximal radial fragment.

Movable component 28 is contoured in such a way that there is a pointed pivotal shelf 81 which includes spot-faced areas 82 and 83 on either side. This shelf 81 is arranged beneath overhanging ledge 84 of stationary component 27. Stationary component 27 also includes two allen head screws 85 and 86 which act on spot-face areas 82 and 83 in order to pivotally change the alignment and orientation of movable component 28 with respect to stationary component 27. These two components rotate relative one to the other by means of pivot pin 87 which is hollow to allow the introduction of allen wrench 105 through components 27 and 28 into the allen head socket of screw 45. Allen head screws 85 and 86 are adjusted, one with respect to the other, to act as stops for the selected rotation of movable component 28 relative to stationary component 27. Once the orientation of component 28 relative to component 27 is set, screws 85 and/or 86 are tightened against spot-faced areas 82 and 83 to lock the selected position of rotation. This selective alignment is illustrated in FIG. 8 and the particular axis of rotation effects the pronation-supination axis of the forearm and therefore of a fracture of the distal radius. It can be seen then that fracture splint 20 is adjustable in a variety of different planes and axes and each one of the various adjustments may be performed relatively separate and independent from each other. For example, a length adjustment between distal member 21 and proximal member 22 may be accomplished by either clockwise or counterclockwise turning of adjustment screw 45. This length adjustment along the longitudinal axis of the radius in no way affects the adjustment in the radial-ulnar deviation plane nor in the pronation-supination axis. Rotational orientation of movable member 26 with respect to stationary member 25 selects the degree of wrist ulnar or radial deviation that is optimal for reduction of a given fracture. Although this adjustment is used to select the degree of radial-ulnar deviation, it has an effect on the overall degree of distraction between the distal member 21 and the proximal member 22, but it has no effect on the rotational orientation of movable member 28 with respect to stationary member 27. The orientation of movable member 28 with respect to stationary member 27 has no substantial influence on the fracture reduction in the planes or about the axes which are primarily the concern of the other two major splint adjustments. Furthermore, the use of two set screws in order to rigidly fix the degree of rotation provides a very reliable and very durable splint setting which is not subject to alignment shift or movement even under adverse conditions. The degree of rigidity of the design makes it virtually impossible for the muscle forces working across the fracture site to affect the orientation of the distal fragment with respect to the proximal fragment once the physician has set fracture splint 20 into proper orientation and alignment.

Now that the apparatus has been fully disclosed, the method of use will be described and discussed. Under adequate anesthesia, the extremity, in this case the right hand of the patient, is prepared and draped in a sterile manner. The second metacarpal base 92 is identified through a short longitudinal incision 93. Care must be taken in order to protect the sensory branches of the radial nerve and avoid the radial artery. The metaphyseal area is identified by either the insertion of the extensor carpi radialis longus tendon or its proximity to the carpo-metacarpal joint. A drill guide 94 which includes a handle member 95, main body portion 96, guide sleeve 97 and pin clearance hole 98 is then utilized in the procedure. The outermost tip of guide sleeve 97 is serrated and is placed firmly onto the bone surface of the second metacarpal base and pin 31 which is approximately ⅛ inch in outside diameter is placed through guide sleeve 97 and is gripped by drill chuck 99. Surgical pin 31 is drilled into the metaphyseal bases of the second (92) and third (100) metacarpals "aiming" toward to the fifth metacarpo-phalangeal joint. Drill guide 94 also includes a second clearance hole 101 which is properly spaced from hole 98 in the event a second surgical pin is to be inserted. If a second pin is required, clearance hole 101 is placed over the first installed pin and the procedure just described is repeated for a second pin.

Figure 4:
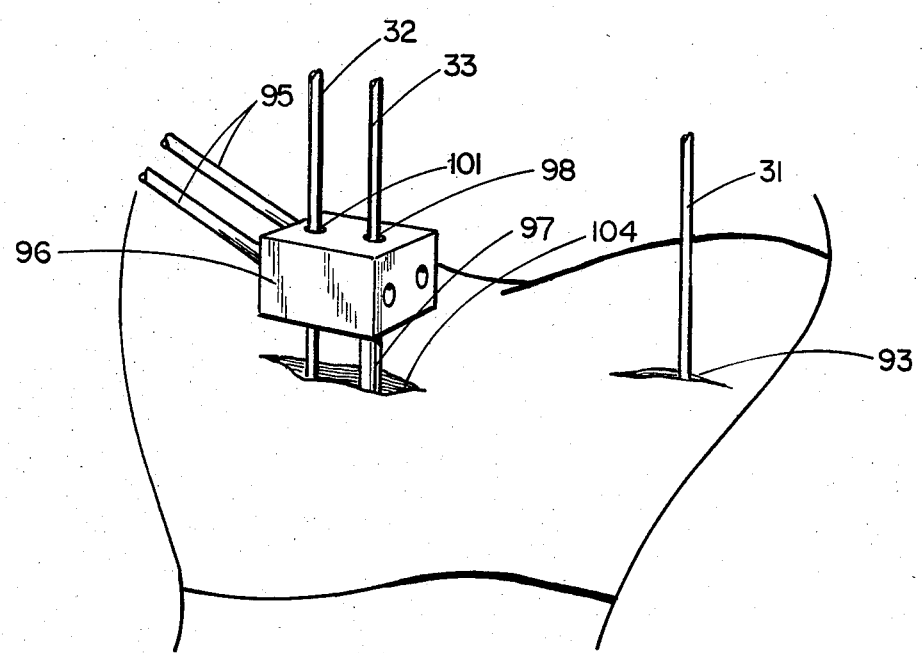
FIG. 4 is a partial perspective view of two surgical pins comprising a portion of the FIG. 1 splint and being inserted into the radial side of the radius shaft.

Once surgical pin 31 has been properly set into the desired orientation through the second and third metacarpals, pins 32 and 33 are inserted into the radius in virtually the same manner as pin 31 was inserted, again utilizing drill guide 94. These pins are inserted into the radial aspect of the radius just proximal to the muscle bellies of the abductor pollicis longus and the extensor pollicis brevis. This relatively bare area on the shaft of the radius can be palpated even on fat forearms with swelling. In order to locate the position of these pins accurately, it is required to first collapse the fracture splint to its shortest length by means of adjustment screw 45 as previously described. This may be done by turning adjustment screw 45 in a counterclockwise direction. Stationary component 25 and movable component 26 are placed in a neutral position with respect to each other as are stationary component 27 and movable component 28. This is done by proper adjusting of the various allen head screws which govern the relative position of the movable components to their corresponding stationary components. Next, the fracture splint 20 is installed onto the distal pin(s) 31 by sliding distal member 21 onto pin 31 by means of hole 34. With the fracture splint 20 slidably received on pin 31, the fractured radius must be manually restored to its proper length by the assisting medical personnel. When this is done, the exterior of the skin overlying the radius approximately ¼ to ½ inch proximal to the proximal extent of the entire device (i.e., the proximal end of stationary component 27) should be marked. This marking estimates the position for the proximal set of pins, 32 and 33. Once the location for pins 32 and 33 is properly marked, the fracture splint 20 is removed from pin 31 and the radius is identified through a short longitudinal incision 104 taking care to protect the sensory branch of the radial nerve. The bare spot on the shaft of the radius for insertion of pins 32 and 33 is identified just volar to the extensor carpi radialis longus muscle. Again, the serrated tip of guide sleeve 97 is placed firmly onto the bone and the first pin is drilled across both corticies of the radius perpendicular to the long axis of the radius. The external threads of the first pin should engage the far cortex firmly. Once the first pin is installed, the drill guide is used as previously described to space and properly orient the second pin. The second pin is then installed in the same manner. In order to obtain proper alignment, when the second pin is being inserted, the handle 95 of the drill guide 94 should be aligned with the long axis of the radius as illustrated in FIG. 4.

Figure 5:
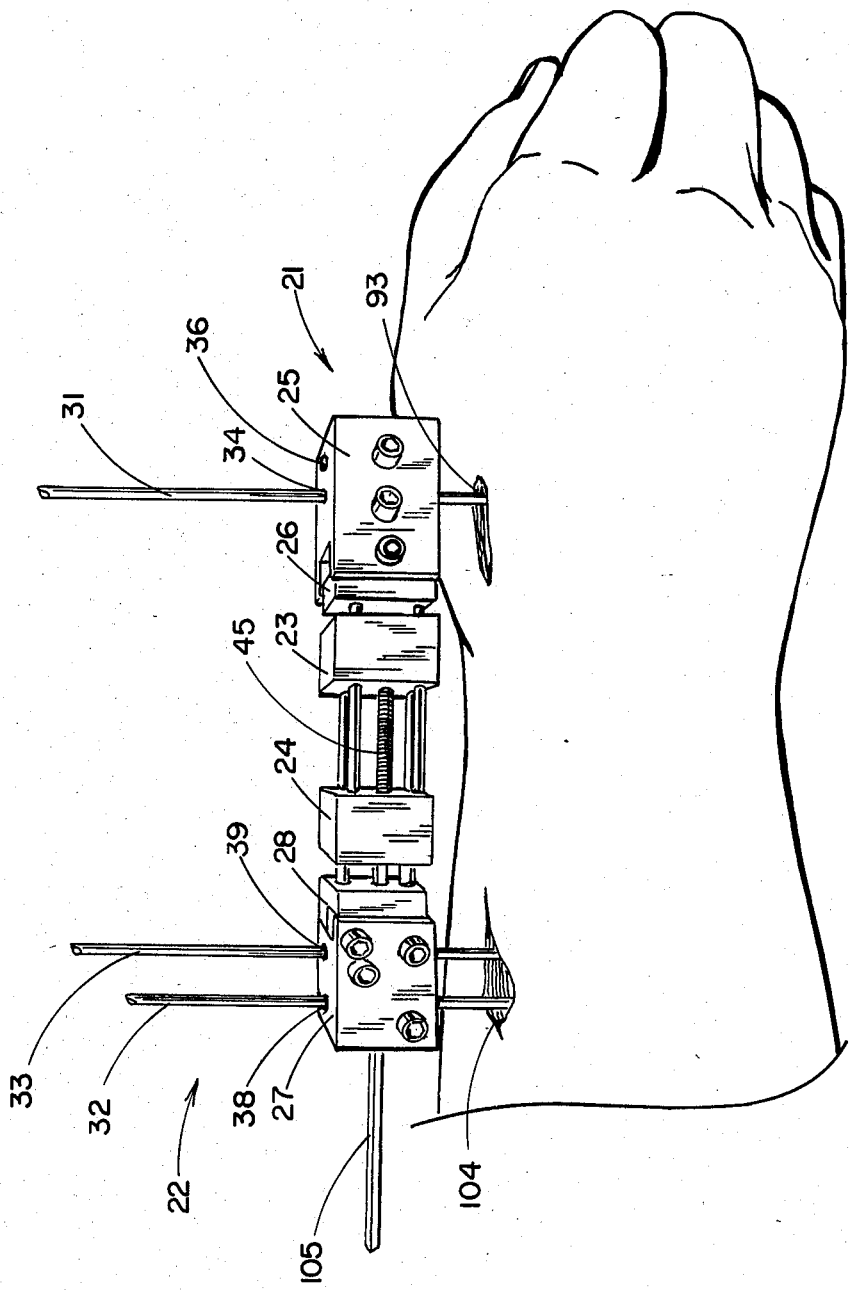
FIG. 5 is a perspective view of the FIG. 1 splint as initially set on a patient's arm.
Figure 6:
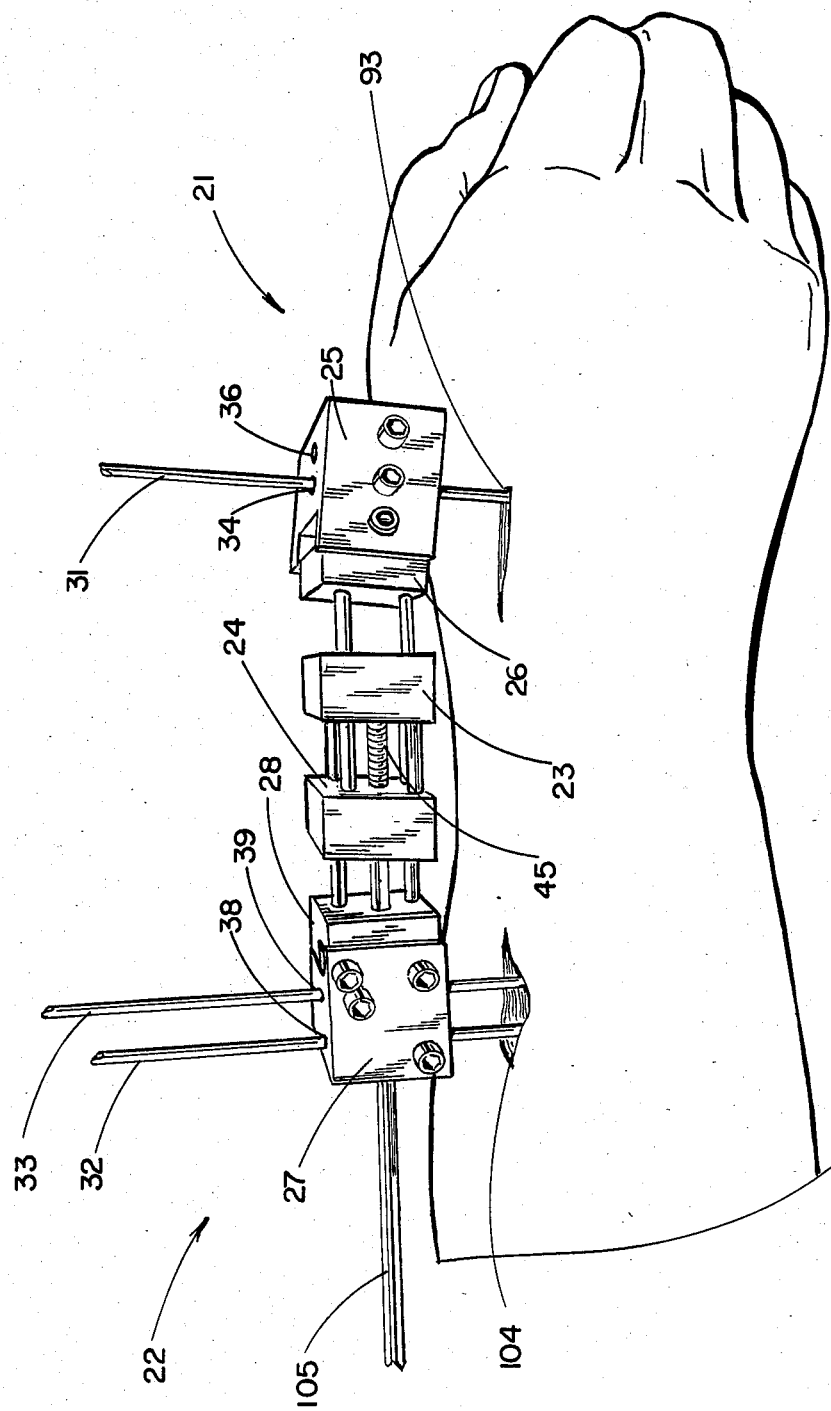
FIG. 6 is a fragmentary, side elevation view of the FIG. 1 splint illustrating restoration of radial length by longitudinal distraction.

Referring to FIG. 5, the first independent adjustment is being performed. It can be seen that block 24 is positioned at its closest point to movable component 28 and block 23 is drawn closely to movable component 26. This represents the shortest overall length of fracture splint 20 and is the starting position when installed on pins 31, 32 and 33. An allen wrench 105 is inserted into the clearance hole in the end of stationary component 27 and inasmuch as this clearance hole coincides with a clearance hole in movable component 28 wrench 105 is capable of reaching the head of adjustment screw 45 such that the distance between distal component 21 and proximal component 22 can begin to be increased. It is important to note that the fracture splint is positioned approximately ¼ to ½ inch above the surface of the skin and prior to any adjustments, the surgical pins have been securely locked in place by means of their corresponding allen head screws at this ¼ to ½ inch spacing. The length adjustment by means of adjustment screw 45 is made with the radial-ulnar deviation in a neutral position, and as allen wrench 105 turns adjustment screw 45 in a clockwise direction, length is restored to the radius as illustrated by FIG. 6. As fracture splint 20 is increased in overall length, incision 93 may experience a slight stretching due to the migration of pin 31 and the incision 93 may have to be extended slightly in order to provide relief. It should be noted that at any point during this surgical procedure X-rays may be taken in order to ascertain the proper alignment and distraction of the distal fragment with respect to the proximal fragment.

The next step is the adjustment of the radial-ulnar deviation and this is performed by means of distal member 21 and the relative orientation of movable component 26 with respect to stationary component 25. As illustrated in FIG. 7 allen wrench 105 is again employed, this time in adjusting screws 63 and 64 so that movable component 26 can be pivoted with respect to stationary component 25 to the desired degree of radial-ulnar deviation. It is a fact that mild degrees of radial or ulnar deviation may facilitate fracture reduction and for this reason, this means of adjustment is critical to a suitable splint device for fractures of the distal radius. It should also be noted that ulnar deviation tends to decrease the distraction force on the fracture site while radial deviation increases distraction forces on the fracture site and ulnar deviation tends to pull the distal pin out of the metacarpal bases while radial deviation of the splint tends to force the metacarpal pins further into the hand. If possible, it is best to select a neutral position with respect to the radial-ulnar deviation although adjustment means as disclosed herein are critical in that a neutral position may not always be suitable.

The final adjustment procedure is illustrated by FIG. 8 wherein allen head screws 85 and 86 are adjusted by means of wrench 105 for pronation of the hand, wrist and distal fragment with respect to the proximal radial fragment. By adjusting screws 85 and 86, the hand is pronated on the forearm which realigns the fracture on its radial border. Of course, the direction which screws 85 and 86 are turned will depend on whether the fracture is of the left hand or right hand. Once the fracture has been properly set, the surgical pins are cut off at a point just external to the distal and proximal members. Then all adjustment screws are securely tightened and tape is applied over the sharp ends of the pins for safety and over the various adjustment screws in order to discourage patient adjustments being made at home or without the care of a physician. It may be preferred to also loosely wrap the forearm with a light bandage. The incision openings are closed in such a manner that pressure or tension is not applied to the surgical pins and the closed incisions are daily cleansed and medicated in order to reduce inflammation and prevent infection. The low profile and light weight of fracture splint 20 permit the splint to be worn comfortably and it may be covered by a coat sleeve so as to be out of sight. The fact that the splint is independently adjustable in three separate planes or axes of alignment provides a unique and specialized device and an improvement to what is known in the art.

Figure 9:
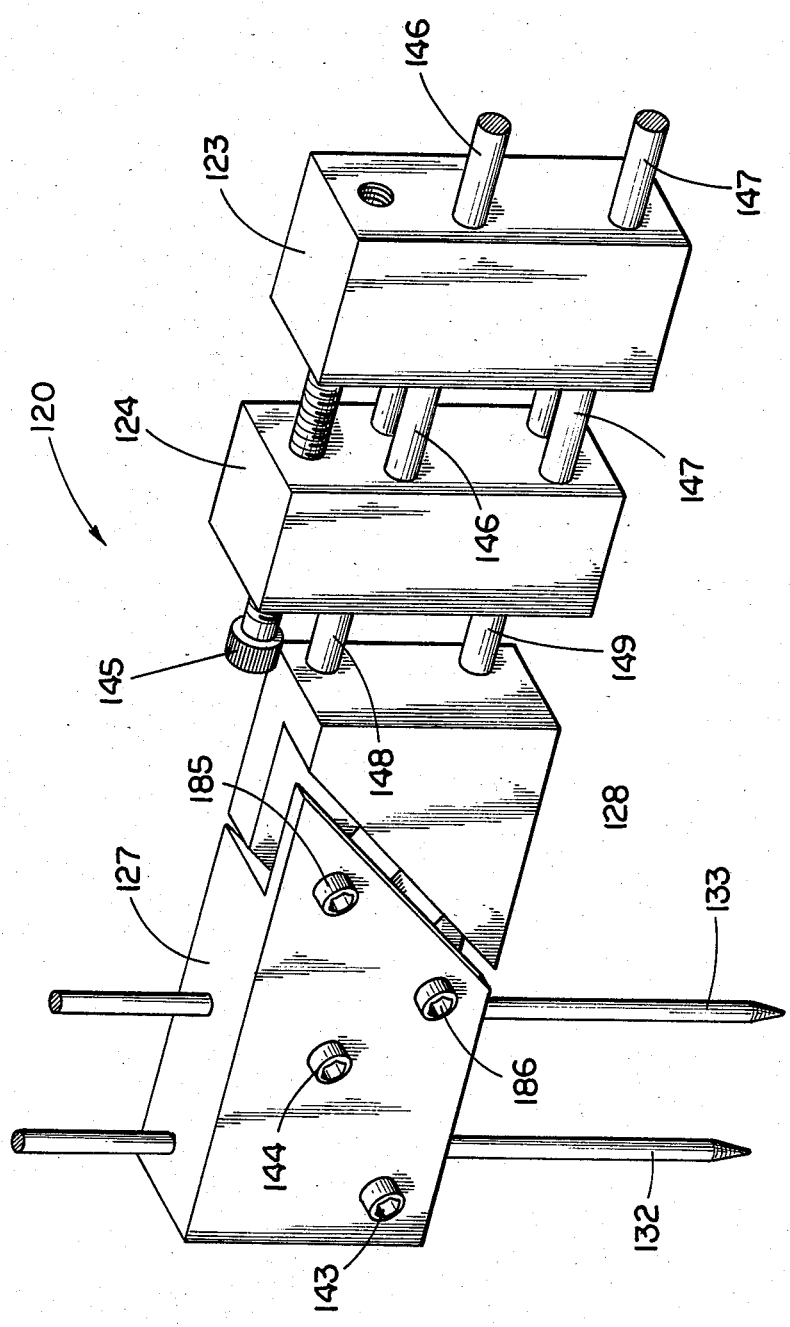
FIG. 9 is a partial perspective view of an alternative fracture splint arrangement according to a typical embodiment of the present invention.
Figure 10:
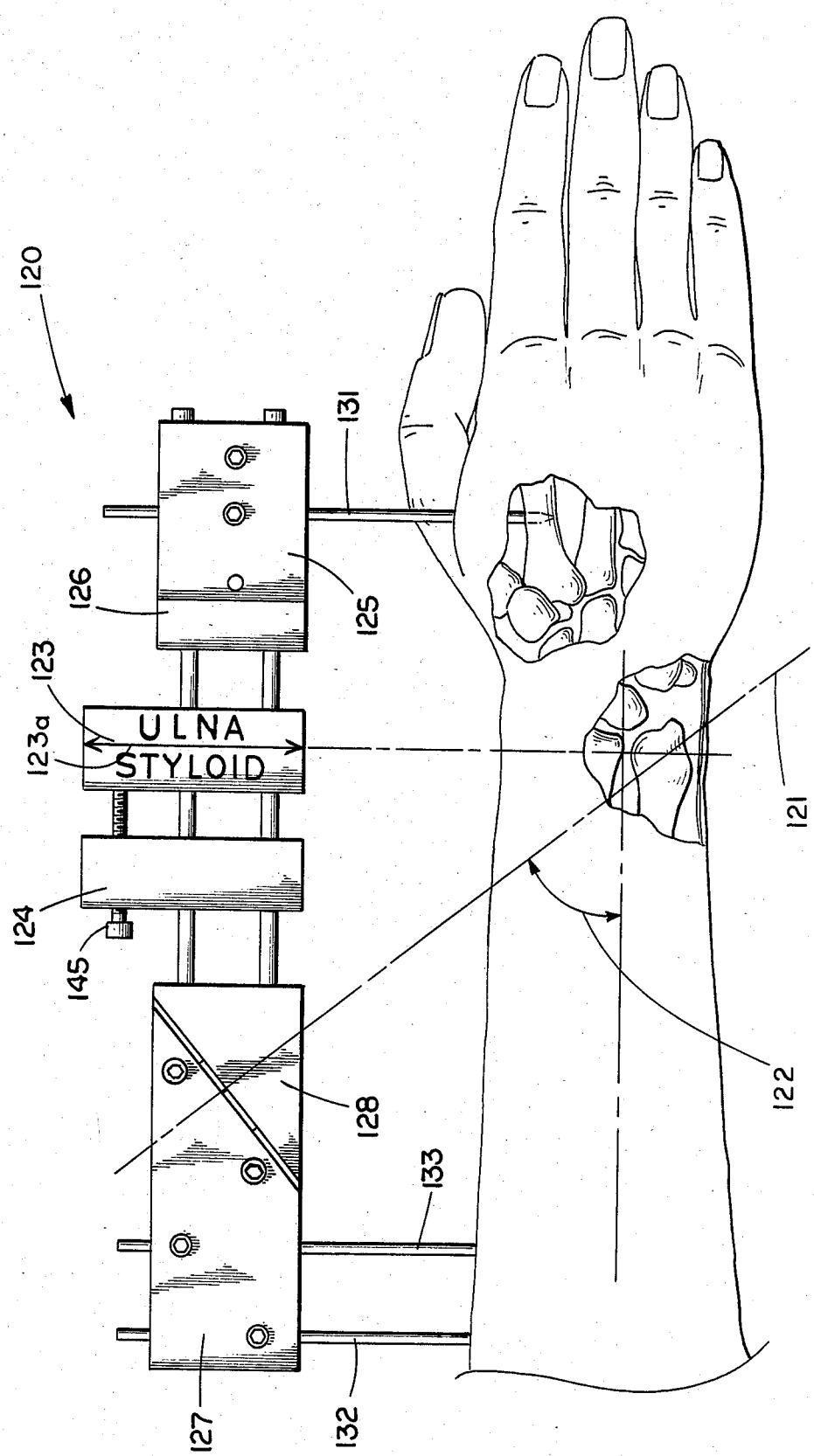
FIG. 10 is a diagrammatic view of the FIG. 9 fracture splint as disposed on a hand and forearm and indicating the axis of rotational movement.

Although the foregoing description fully discloses the situation wherein the axis of rotation, that occurring between members 27 and 28, is substantially parallel to the longitudinal axis of the forearm, an alternative arrangement is also envisioned. It is to be stressed that while either arrangement is a significant improvement over prior devices, the alternative arrangement which follows is preferred as it establishes the rotational axis of the fracture splint about an axis that projects through the axis of the rotational evolution of the fracture, the radial aspect of the distal ulna. In practice, this allows pronation of the distal fragment with respect to the proximal fragment by rotating member 127 with respect to member 128 without adversely affecting the degree of dorsal displacement of the distal fragment with respect to the proximal fragment. This alternative arrangement 120 is illustrated by FIGS. 9 and 10 wherein the axis of rotation, now between members 127 and 128 (indicated by line 121), extends from the radius side of the arm through the arm at an angle 122 of approximately 35 to 40 degrees with respect to the longitudinal axis of the radius in a plane separating dorsal from volar, to a point of intersection near the styloid process of the ulna. In order to achieve this particular axis of rotation, members 127 and 128, although functionally similar to members 27 and 28, must be modified structurally so as to provide for pins 132 and 133 and for rods 148 and 149. A comparison of FIG. 9 with FIG. 2 will reveal the differences between the two pairs of members and FIG. 10 illustrates the imaginary line 121 indicating this axis of rotation. Similar component pieces have been numerically identified by increasing the corresponding reference numeral by 100.

A further change of this alternative arrangement is that access to the head of screw 145 is no longer available through members 127 and 128 due to the angle of the pivot pin since the axis of this pin must now coincide with line 121. Consequently, members 123 and 124 include an offset portion along their top edge which receives screw 145. This offset portion could equally well be disposed along either side so long as the head of the screw is accessible to the allen wrench.

The need for this alternative arrangement is due to the fact that with severe fractures, the human anatomy is such that as the distal fragment of the radius is rotated with respect to the proximal fragment of the radius, the distal fragment needs to be displaced volarly while the proximal fragment is simultaneously displaced dorsally. With the rotational axis of the splint substantially parallel to the axis about which the fracture supinates, yet spaced two to three inches apart, as is disclosed for the first embodiment form, rotation between members 27 and 28 increases the dorsal displacement of the distal fragment. This result is a primary concern with severely displaced fractures and thus the need for the alternative form of FIGS. 9 and 10. A further change which facilitates the utilization of this alternative form is to increase the spacing between pins 132 and 133 over that of pins 32 and 33. Also, by locating pins 132 and 133 on a common centerline with pin 131 (or pins 131) when the splint is in a neutral position, a single splint is suitable for the left arm as well as for the right arm. To assure this versatility, it is necessary for all the pins to be equidistant between dorsal and volar aspects of the splint.

FIG. 10 also illustrates an additional feature which is provided to facilitate the proper positioning of the proximal set of pins 132 and 133. It is to be understood that this feature, the markings on block 123, would also be provided as part of block 23 if desired, there being no difference between the two embodiments as to this marking feature. Block 123 is provided with an arrow marking 123a and the words "Ulna" and "Styloid." This arrow marking continues downwardly across both ends of block 123 and is to be generally aligned with the position of the ulnar styloid process. With the splint in any position (contracted or expanded), this arrow marking is used to properly position the splint relative to the particular anatomy so that the location for the proximal set of pins can be quickly and easily determined. It is also envisioned to provide two arrow markings on the same block in parallel yet spaced apart relationship to each other. One of these arrow markings would be for larger hands and the other for smaller hands.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

The invention claimed is:

1. A splint for setting fractures of the radius, said splint comprising:
   a distal member;
   first means for securing said distal member to a metacarpal bone on the distal side of the radius fracture;
   a proximal member having a stationary component, a movable component, and a pivot pin pivotally joining the movable component to said stationary component;
   second means for securing the stationary component of said proximal member to the radius on the proximal side of the radius fracture; and
   elongated means for joining said distal member to said proximal member, said joining means including means for selectively varying the distance of separation between said distal member and said proximal member, said pivot pin being at an acute angle with respect to the longitudinal axis of said elongated means and being coextensive with a line extending from the radius side of the arm at an acute angle relative to the longitudinal axis of the radius to a point of intersection near the styloid process of the ulna.

* * * * *